United States Patent [19]
Edmark et al.

[11] Patent Number: 5,800,503
[45] Date of Patent: Sep. 1, 1998

[54] APPARATUS AND METHOD FOR PRODUCING ELECTRICAL STIMULATION IN RESPONSE TO AN AUDIO SIGNAL

[75] Inventors: Tomima L. Edmark; Roland W. Gooch, both of Dallas, Tex.

[73] Assignee: SWAK Ventures, Inc., Dallas, Tex.

[21] Appl. No.: 649,264

[22] Filed: May 17, 1996

[51] Int. Cl.⁶ .................................................. A61N 1/00
[52] U.S. Cl. .................................. 607/145; 600/27
[58] Field of Search .......................... 607/145, 46, 48, 607/54, 56; 600/26-28

[56] References Cited

U.S. PATENT DOCUMENTS

| | | |
|---|---|---|
| 524,120 | 8/1894 | Speare . |
| 1,046,985 | 12/1912 | Creedon . |
| 1,266,393 | 5/1918 | Bowen . |
| 1,539,299 | 5/1925 | Cheney . |
| 2,100,234 | 11/1937 | Belknap ............................ 128/24.5 |
| 2,336,426 | 12/1943 | Trotta ................................ 128/406 |
| 3,035,571 | 4/1962 | Jones ................................. 128/32 |
| 3,556,105 | 1/1971 | Shepard ............................ 128/417 |
| 4,033,356 | 7/1977 | Hara .................................. 128/405 |
| 4,309,030 | 1/1982 | Goldfarb et al. ................. 273/1 GC |
| 4,503,863 | 3/1985 | Katims ............................ 600/26 X |
| 4,585,005 | 4/1986 | Lue et al. ...................... 128/419 R |
| 4,909,263 | 3/1990 | Norris .............................. 128/788 |
| 4,976,264 | 12/1990 | Petrofsky ........................ 128/421 |
| 5,012,816 | 5/1991 | Lederer ........................... 128/735 |
| 5,076,281 | 12/1991 | Gavish .......................... 600/28 X |
| 5,086,788 | 2/1992 | Castel et al. .................... 128/800 |
| 5,213,338 | 5/1993 | Brotz ............................... 273/460 |
| 5,476,504 | 12/1995 | Paolizzi .......................... 607/150 |
| 5,482,277 | 1/1996 | Young ............................. 273/161 |

OTHER PUBLICATIONS

Hugh Morris, "The Art of Kissing," Source Unknown, Copyright 1936, 14 pages.

*Primary Examiner*—Jennifer Bahr
*Assistant Examiner*—Ryan Carter
*Attorney, Agent, or Firm*—Baker & Botts, L.L.P.

[57] ABSTRACT

An apparatus (2) is provided for producing electrical stimulation to at least one person (10a, 10b) in response to a varying output audio signal (4). The apparatus (2) includes a first circuit (13) which receives the varying output audio signal (4). A second circuit (20), coupled to the first circuit (13), generates a plurality of electrical pulses which vary in response to the varying output audio signal (4). A node (8a, 8b) is coupled to the second circuit (20). The node (8a, 8b) conducts the electrical pulses in order to provide a pleasing variable stimulus to the person (10a, 10b) when the person (10a, 10b) contacts the node (8a, 8b).

15 Claims, 3 Drawing Sheets

APPARATUS AND METHOD FOR PRODUCING ELECTRICAL STIMULATION IN RESPONSE TO AN AUDIO SIGNAL

TECHNICAL FIELD OF THE INVENTION

This invention relates in general to stimulation devices, and more particularly to an apparatus and method for producing electrical stimulation in response to an audio signal. The apparatus includes a first circuit operable to receive an audio signal, a second circuit coupled to the first circuit and operable to generate pulses which vary in response to the varying audio signal and two nodes coupled to the second circuit. A pulse is conducted through a current conducting circuit to stimulate a person touching one node and a second person touching the other node.

BACKGROUND OF THE INVENTION

Music has often been employed to enhance the mood of a romantic setting, thus stirring people to physical contact, such as kissing. Although this physical contact can be enjoyable on its own, the pleasure of a kiss could be further enhanced if other stimulation was applied in conjunction with the music.

It has been previously known to provide small electrical stimulation to patients as therapy, or even to persons as a novelty. However, it has not been previously known to provide electrical stimulation in conjunction with the playing of music in order to heighten romantic feelings, nor to provide such romantic electrical stimulation to two people in a romantic situation such as kissing.

SUMMARY OF THE INVENTION

Accordingly, a need has arisen for enhancing the enjoyment of music and for also enhancing the physical contact between two people.

According to an embodiment of the present invention, an apparatus is provided for producing electrical stimulation to at least one person in response to a varying output audio signal. The apparatus includes a first circuit which receives the varying output audio signal. A second circuit, coupled to the first circuit, generates a plurality of electrical pulses which vary in response to the varying output audio signal. A node is coupled to the second circuit. The node conducts the electrical pulses in order to provide a pleasing variable stimulus to the person when the person contacts the node.

According to another embodiment of the present invention, an apparatus is provided for producing electrical stimulation at a point of contact between at least a first person and a second person. The apparatus includes a first circuit which receives a varying output audio signal. A second circuit, coupled to the first circuit, generates a plurality of electrical pulses which vary in response to said varying output audio signal. A first node and a second node are coupled to the second circuit. The first and second nodes conduct the electrical pulses through a current conducting circuit created when the first person touches the first node and makes contact with the second person touching the second node, thereby providing a pleasing variable stimulus to the first and second persons at the point of contact.

According to yet another embodiment of the present invention, a method is provided for producing electrical stimulation to a person. The method includes the following steps: receiving a varying output audio signal from an audio device; generating a varying electrical pulse signal in response to said varying audio output signal; and conducting the varying electrical pulse signal to a node in order to provide a pleasing variable stimulus to the person when the person contacts the node.

Important technical advantages of the present invention include generating electrical pulses in response to an output signal from an audio device in order to enhance physical contact between two people. In one embodiment, this is accomplished by generating an electrical pulse each time that a voltage of the output audio signal exceeds a predetermined threshold. The electrical pulses appear at a first hand piece which may be held by a first person and a second hand piece which may be held by a second person. When the first and second persons make contact, an electrical circuit is formed so that the electrical pulses can be felt at the point of contact. Other technical advantages are readily apparent to one skilled in the art from the following figures, description, and claims.

BRIEF DESCRIPTION OF THE DRAWINGS

For a more complete understanding of the present invention, and for further features and advantages thereof, reference is now made to the following description taken in conjunction with the accompanying drawings, in which.

DETAILED DESCRIPTION OF THE INVENTION

Figure 1:
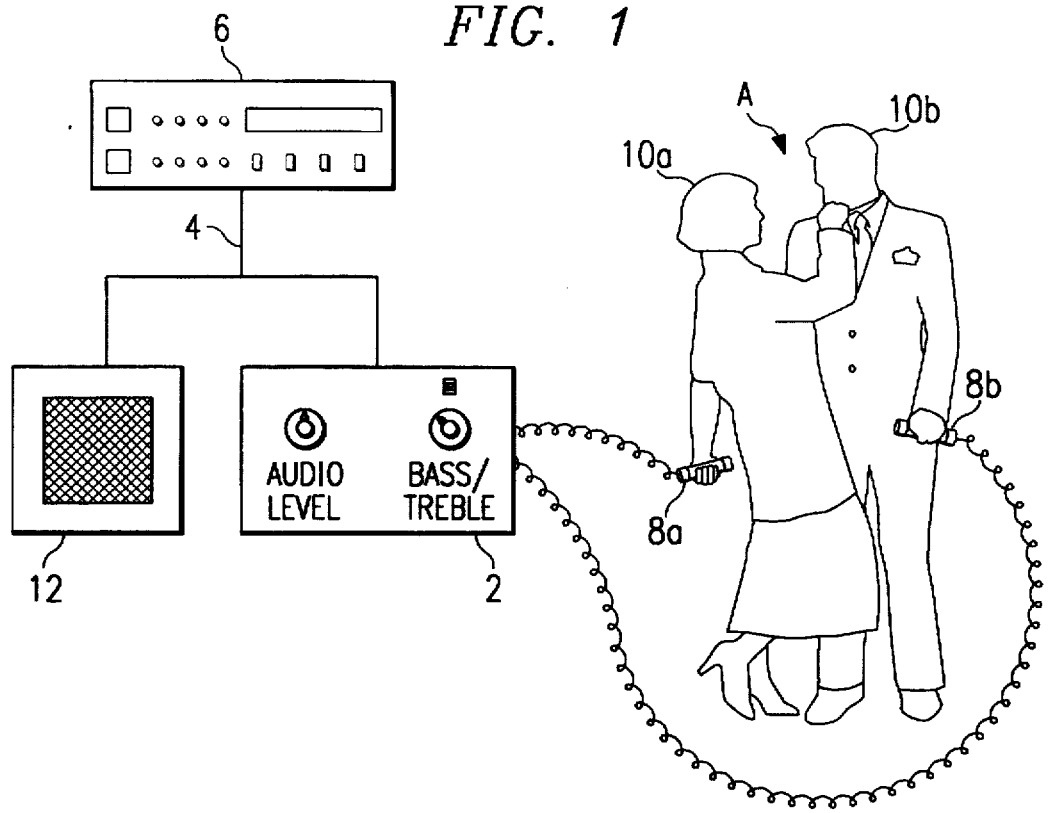
FIG. 1 illustrates an apparatus for producing electrical stimulation at a point of contact between a first person and a second person.

FIG. 1 illustrates an apparatus 2 for producing electrical stimulation in response to an output audio signal 4. Apparatus 2 is coupled to and can receive output audio signal 4 from an audio device 6.

Output audio signal 4 may correspond to a song, a musical composition, a speech, or any other stimulus that can be heard. The voltage of output audio signal 4, which can range from a fraction of a volt up to 20 volts, may vary with time according to the highs and lows of the corresponding audible stimulus. For example, for a symphonic work, the voltage may increase with a crescendo in the music and decrease with a decrescendo. Likewise, a cymbal crash may be characterized by a particularly large voltage in output audio signal 4.

Apparatus 2 functions to modulate a pulse signal according to the varying voltage of output audio signal 4, thus outputting a plurality of voltage pulses. The voltage pulses can be relayed to a first node or hand piece 8a and a second node or hand piece 8b. First and second hand pieces 8a and 8b, which can be formed in part from metal or any other conductive material, may include a dial, a switch, a slide, or any other suitable control for adjusting the magnitude of the voltage pulses appearing at the hand pieces. First and second hand pieces 8a and 8b can be contacted or held by persons 10a and 10b, respectively, or, alternatively, by a single person 10. It should be understood that contact between a person and a node is not limited only to holding, but also includes any other suitable contact. For example, a node could be attached to a person's body by adhesive.

Audio device 6 can be a stereo system, a radio, a compact disc player, a tape cassette player, a phonograph, or any other device operable to output an output audio signal 4. Audio device 6 can be coupled to or may include a speaker 12. Speaker 12 functions to receive output audio signal 4 and, in response, generate the audible stimulus corresponding to output audio signal 4.

In operation, output audio signal 4 causes the audible stimulus, which can be heard by first person 10a and a second person 10b, to emanate from speaker 12. Concurrently, output audio signal 4 is received by apparatus 2. Apparatus 2 outputs one or more voltage pulses, which are then relayed to hand pieces 8. In one case, first person 10a holds hand piece 8a and second person 10b holds hand piece 8b. When first person 10a and second person 10b make contact, such as by kissing, holding hands, or any other suitable method of contact, an electrical circuit is completed and the voltage pulses produce stimulation at the point of contact, indicated by arrow A, in conjunction with the audio stimulus. For kissing, apparatus 2 produces a very pleasant, varying stimulation in the mouths of users. Consequently, contact between the first and second persons 10 is enhanced by apparatus 2. In another case (not shown), a single person 10 may hold both hand pieces 8. Apparatus 2 provides a pleasing variable stimulus to the person 10.

The following describes primarily how one embodiment of apparatus 2 produces electrical stimulation by generating an electrical pulse each time that the voltage magnitude of output audio signal 4 exceeds a predetermined threshold. However, it should be understood that the present invention is not limited to such an exemplary embodiment.

Figure 2:
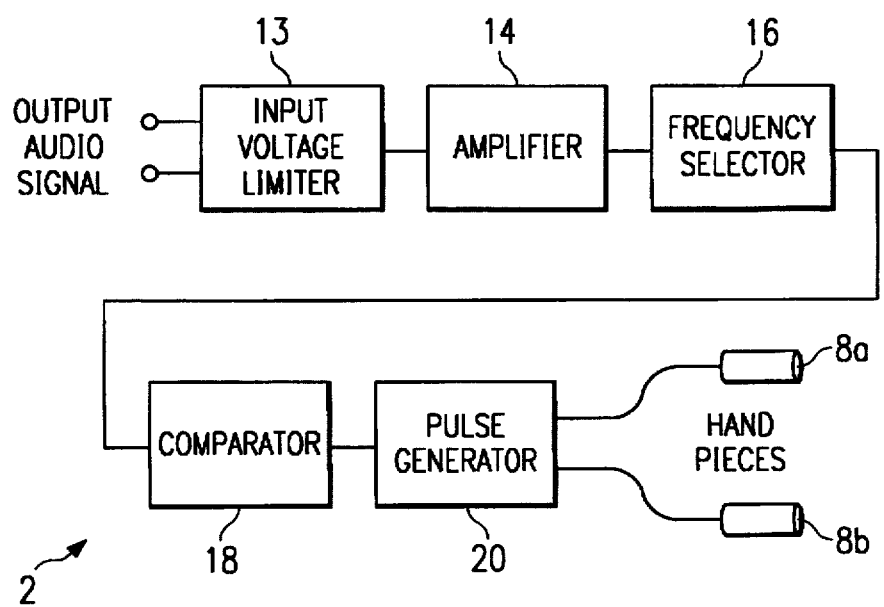
FIG. 2 is a block diagram of one embodiment of the apparatus shown in FIG. 1.

FIG. 2 is a block diagram of one embodiment of the apparatus 2 shown in FIG. 1. In this embodiment, apparatus 2 includes an input voltage limiter 13. Input voltage limiter 13 can receive output audio signal 4 from audio device 6. Input voltage limiter 13 limits the voltage of output audio signal 4 to a level, such as 0.6 volts, that is not harmful or destructive to apparatus 2.

An amplifier 14 is coupled to input voltage limiter 13. Amplifier 14 amplifies the signal output by input voltage limiter 12. Consequently, even if output audio signal 4 is particularly weak, apparatus 2 is still able to produce electrical stimulation in response.

A frequency selector 16, coupled to amplifier 14, receives the amplified signal. The audio stimulus corresponding to output audio signal 4 may include many frequencies of sound, ranging from bass to treble. Each frequency or range of frequencies may be characterized by its own distinct voltage signal in output audio signal 4. For example, low frequencies may have a separate voltage signal from the high frequencies. Frequency selector 16 allows a user of apparatus 2, such as first person 10a or second person 10b, to select which frequency or range of frequencies in the audio stimulus produces electrical stimulation. For example, a user may select bass frequencies or, alternatively, treble frequencies. Frequency selector 16 outputs the voltage signal only for the portion of the audio stimulus within the selected frequency or range of frequencies.

A comparator 18 is coupled to frequency selector 16. Comparator 18 receives the voltage signal corresponding to the selected frequency or range of frequencies and compares the magnitude of the voltage in the signal against a predetermined reference or threshold voltage. Comparator 18 is able to detect whenever the voltage magnitude of the signal exceeds the predetermined threshold voltage.

A pulse generator 20 is coupled to comparator 18. Pulse generator 20 generates a voltage pulse in response to each detection by comparator 18 of a voltage magnitude that exceeds the threshold voltage. These voltage pulses generated by pulse generator 20 may have a predefined voltage magnitude, such as 75 volts.

Hand pieces 8a and 8b are coupled to pulse generator 20. Each hand piece 8 can be held by a person 10. Hand pieces 8a and 8b may include a control for adjusting the magnitude of the voltage appearing at the hand pieces.

In the operation for this embodiment of apparatus 2 illustrated in FIG. 2, output audio signal 4 is received at input voltage limiter 13. Input voltage limiter 13 limits the voltage of the signal to a safe level for apparatus 2. If output audio signal 4 is weak, amplifier 14 may amplify the voltage of the signal. Using frequency selector 16, first person 10a or second person 10b can select a particular frequency or range of frequencies in the audio stimulus. Comparator 18 detects each instance when the voltage magnitude of the signal corresponding to the selected frequency or range of frequencies exceeds the predetermined threshold voltage. In response to each detection, pulse generator 20 outputs a voltage pulse, which is then relayed to hand pieces 8. First person 10a holds hand piece 8a and second person 10b holds hand piece 8b. When first person 10a and second person 10b make contact, an electrical circuit is completed and the voltage pulses produce stimulation at the point of contact in conjunction with the audio stimulus. Consequently, contact between the first and second persons is enhanced.

Figure 3:
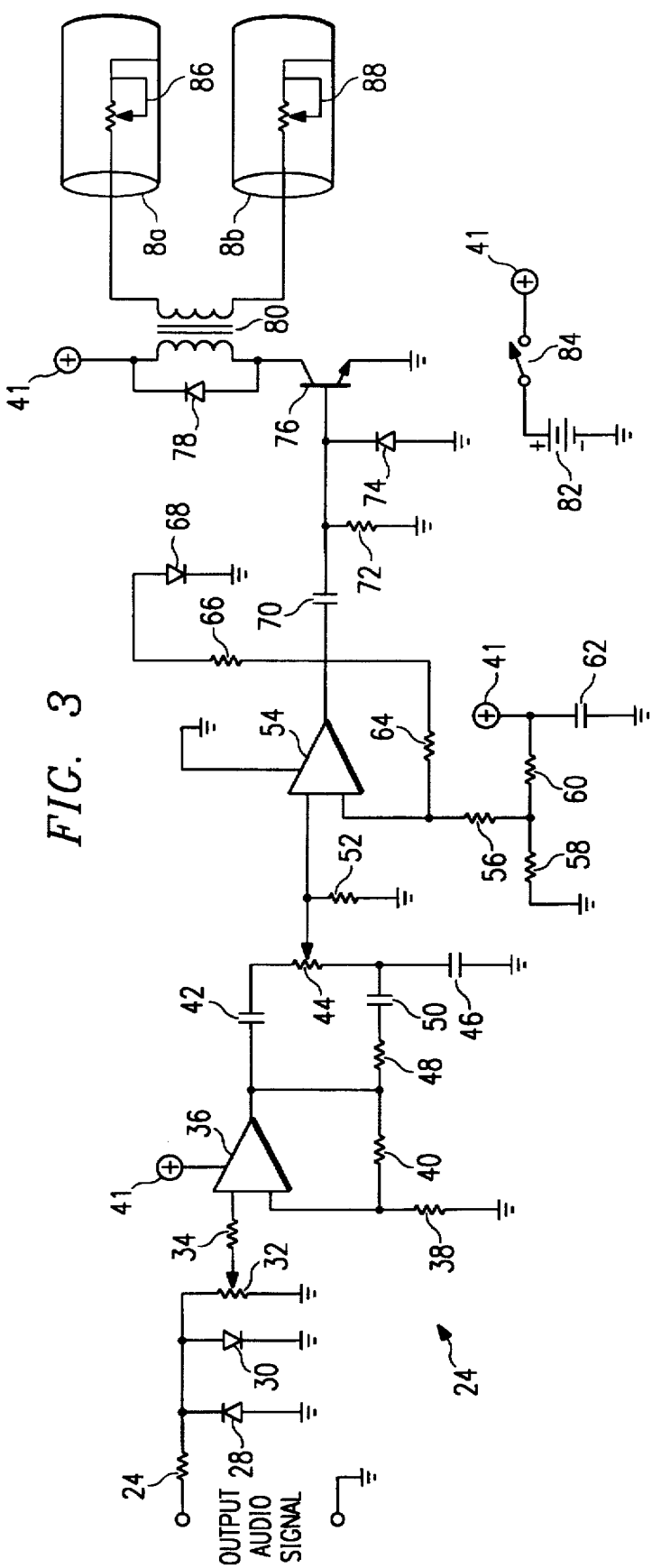
FIG. 3 is a schematic diagram of an exemplary circuit for the embodiment of the apparatus shown in FIG. 2.

FIG. 3 is a schematic diagram of an exemplary circuit 24 for the embodiment of apparatus 2 shown in FIG. 2. Various portions of circuit 24 correspond to the elements of the embodiment of apparatus 2 described above. Thus, in circuit 24, input voltage limiter 13 can be implemented as follows. A resistor 24, which may have a value of 270 ohms, is connected to one node at which an output audio signal is received. The other node is connected to ground. A diode 28, a diode 30, and a potentiometer 32 are connected in parallel between resistor 24 and ground. Potentiometer 32 may have a value of 1K ohms.

Amplifier 14 includes a resistor 34, which is coupled to potentiometer 32 in voltage limiter 13. Resistor 34 may have a value of 1K ohms. A first input of an operational amplifier (OP AMP) 36 is connected to resistor 34. A second input for OP AMP 36 is coupled to a resistor 38 which is connected to ground. Resistor 38 may have a value of 1K ohms. The output of OP AMP 36 is coupled to the OP AMP's second input by a resistor 40, which can have a value of 33K ohms. The OP AMP is coupled to a voltage source 41.

Frequency selector circuit 16 includes a capacitor 42, which is coupled to the output of OP AMP 36 in amplifier 14. Capacitor 42 may have a value of 1500 picofarads. A potentiometer 44 and a capacitor 46 are coupled in series between capacitor 42 and ground. Potentiometer 44 may have a value of 100K ohms; capacitor 46 may have a value of 0.01 microfarad. A resistor 48 and a capacitor 50 are coupled in series between the output of OP AMP 36 and capacitor 46. Resistor 48 may have a value of 100K ohms. Capacitor 50 may have a value of 0.1 microfarad.

Comparator 18 may be implemented as follows. A resistor 52, which may have a value of 100K ohms, is coupled between potentiometer 44 of frequency selector circuit 16 and ground. A first input of an OP AMP 54 is also coupled to potentiometer 44. A resistor 56 and a resistor 58 are coupled in series between a second input of OP AMP 54 and ground. Resistor 56 and resistor 58 may have values of 1.5K and 1K ohms, respectively. A resistor 60, which may have a value of 3.9K ohms, is coupled between the connection of resistors 56 and 58 and voltage source 41. Resistor 60 and resistor 58 determine the reference threshold voltage for comparator 18. A capacitor 62, which may have a value of 220 microfarads, is coupled between voltage source 41 and ground. Capacitor 62 serves to stabilize the power supply voltage during operation. The output of OP AMP 54 is connected to the second input of the OP AMP by a resistor 64, which may have a value of 220K ohms. Resistor 64 and resistor 56 determine the gain of comparator 18. A resistor 66 and a light-emitting diode 68 are coupled in series between the output of OP AMP 54 and ground. Light-emitting diode 68 functions to indicate that voltage pulses are being generated. Resistor 66 may have a value of 1200 ohms.

Pulse generator 20 includes a capacitor 70 connected to the output of OP AMP 54 in comparator 18. Capacitor 70 may have a value of 0.1 microfarad. A resistor 72 and a diode 74 are coupled in parallel between capacitor 70 and ground. Resistor 72 may have a value of 2K ohms. The base of a transistor 76 is also connected to capacitor 70. The emitter of transistor 76 is connected to ground. A diode 78 and one side of a step-up transformer 80 are coupled in parallel between voltage source 41 and the collector of transistor 76. The other side of transformer 80 is coupled at one end to hand piece 8b and at the other end to hand piece 8a.

Potentiometers 86 and 88 are contained within hand pieces 8a and 8b, respectively. Potentiometers 86 and 88 may each have a value of 100K ohms. Potentiometers 86 and 88 allow a user or users of apparatus 2 to adjust the magnitude of voltage pulses appearing at hand pieces 8a and 8b.

A battery 82 may serve as the voltage source 41 for circuit 24 when a switch 84 is closed.

Figure 4:
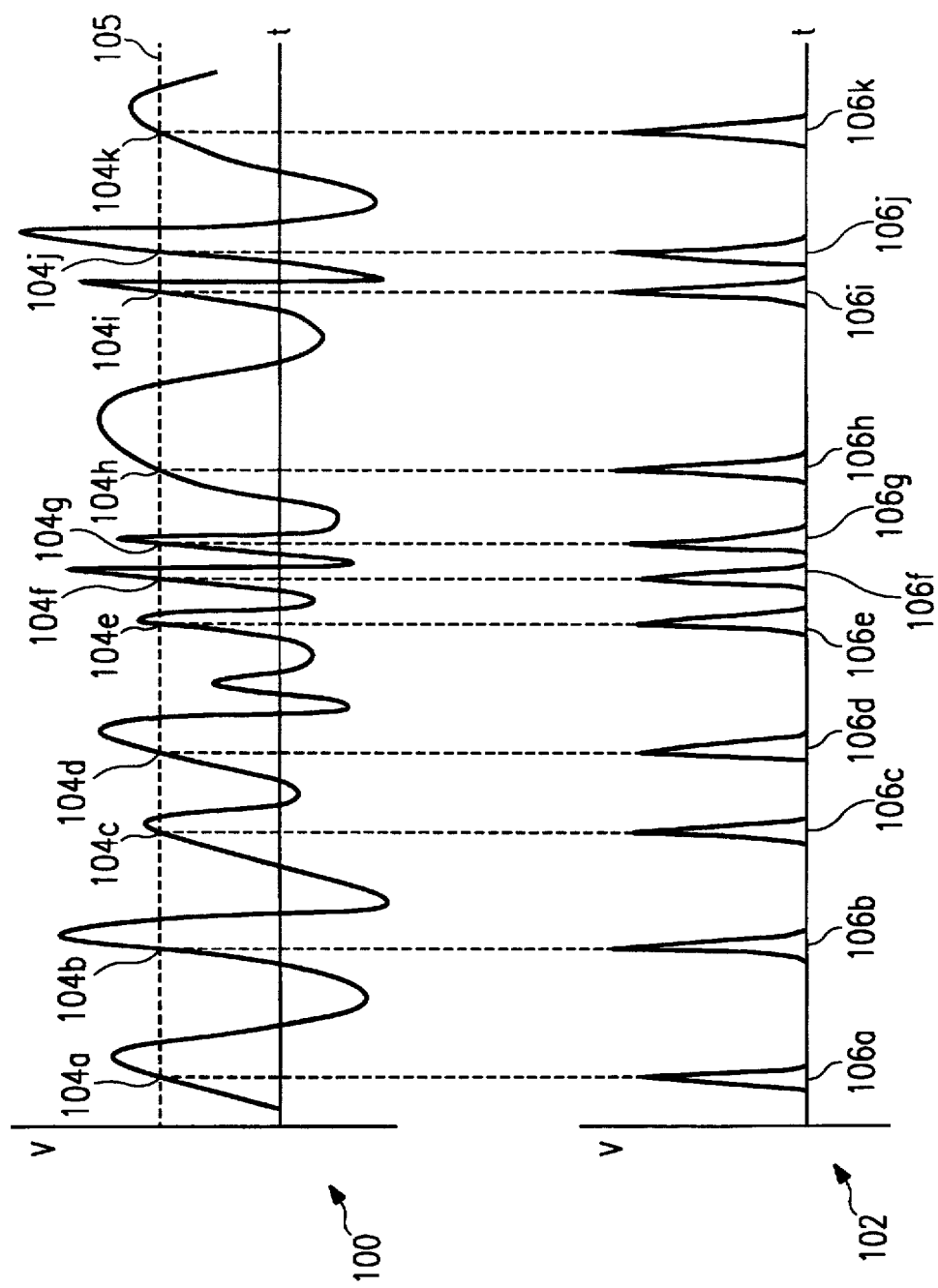
FIG. 4 illustrates a pulse signal output by the embodiment of apparatus shown in FIG. 2 in response to an exemplary output audio signal.

FIG. 4 illustrates an exemplary output audio signal 100 that may be received by apparatus 2 and a corresponding pulse signal 102 output by the embodiment of apparatus 2 shown in FIG. 2 in response to exemplary output audio signal 100.

Exemplary output audio signal 100 is a voltage output corresponding to a certain frequency or range of frequencies in an audio stimulus. The voltage varies with time according to the highs and lows of the audio stimulus at the frequency or range of frequencies. For example, each "peak" in exemplary output audio signal 100 may correspond to a cymbal crash or similar loud sound in the audio stimulus. Each "valley" in exemplary output audio signal 100 may correspond to a moment in which a sound at the particular frequency or range of frequencies is inaudible or barely audible in the audio stimulus. The magnitude of the voltage of exemplary output audio signal 100 may exceed a predetermined threshold voltage level 105 at a plurality of points 104a–104k.

Pulse signal 102 comprises a plurality of voltage pulses 106a–106k. These voltage pulses 106 are generated by apparatus 2 whenever the voltage magnitude of exemplary output audio signal 100 exceeds the predetermined threshold voltage level 105. Consequently, a voltage pulse 106 appears in pulse signal 102 for each of points 104a–104k. Voltage pulses 106 can have a constant magnitude, such as 75 volts. When applied at hand pieces 8a and 8b, these voltage pulses 106 produce electrical stimulation at the point of contact between first person 10a and second person 10b holding a respective hand piece 8.

Although the present invention and its advantages have been described in detail, it should be understood that various changes, substitutions, and alterations can be made therein without departing from the spirit and scope of the invention as defined by the appended claims.

What is claimed is:

1. An apparatus for producing electrical stimulation at a point of contact between at least a first person and a second person, comprising:
    a first circuit operable to receive a varying output audio signal;
    a second circuit coupled to the first circuit and operable to generate a plurality of electrical pulses which vary in response to said varying output audio signal;
    a first node and a second node coupled to the second circuit and operable to conduct the electrical pulses through a current conducting circuit created when the first person touches the first node and makes contact with the second person touching the second node, thereby providing a pleasing variable stimulus to the first and second persons at the point of contact;
    a first control coupled to the first node and operable to adjust a magnitude of the electrical pulses appearing at the first node; and
    a second control coupled to the second node and operable to adjust a magnitude of the electrical pulses appearing at the second node.

2. The apparatus of claim 1, further comprising a third circuit coupled to the second circuit and operable to select a voltage signal in the output audio signal corresponding to a particular range of frequencies in an audio stimulus associated with the output audio signal.

3. The apparatus of claim 1, wherein the second circuit is operable to modulate a pulse signal in response to a varying voltage magnitude of the output audio signal.

4. The apparatus of claim 1, further comprising a fourth circuit operable to detect a predetermined voltage magnitude in the output audio signal.

5. The apparatus of claim 1, wherein each of the first and second nodes comprises a hand piece.

6. The apparatus of claim 1, further comprising a fifth circuit coupled to the first circuit and operable to amplify the output audio signal.

7. The apparatus of claim 1, wherein the first circuit is further operable to limit the voltage of the output audio signal to a maximum of 0.6 volts.

8. A method for producing electrical stimulation at a point of contact between at least a first person and a second person, comprising the steps of:
    receiving a varying output audio signal from an audio device;
    selecting a signal of a predetermined frequency from said varying output audio signal;
    generating a varying electrical pulse signal in response to said selected signal of predetermined frequency; and
    conducting the varying electrical pulse signal through a circuit formed by contact between the first person and the second person in order to provide a pleasing variable stimulus to the first and the second persons.

9. The method of claim 8, further comprising the step of detecting a predetermined voltage magnitude in the output audio signal.

10. The method of claim 8, wherein the step of generating a varying electrical pulse signal comprises modulating a voltage signal in response to a varying voltage magnitude of the output audio signal.

11. A method for producing electrical stimulation at a point of contact between at least a first person and a second person, comprising the steps of:

receiving a varying output audio signal from an audio device;

generating a varying electrical pulse signal from an internal power source in response to said varying output audio signal; and conducting the varying electrical pulse signal through a circuit formed by contact between the first person and the second person in order to provide a pleasing variable stimulus to the first and second persons.

12. The method of claim 11, further comprising the step of amplifying the output audio signal.

13. The method of claim 11, further comprising the step of detecting a predetermined voltage magnitude in the output audio signal.

14. The method of claim 11, further comprising the step of selecting a predetermined frequency.

15. An apparatus for producing electrical stimulation to at least a first person and a second person, comprising:

a first circuit operable to receive a varying output audio signal;

a second circuit coupled to the first circuit and operable to generate a plurality of electrical pulses which vary in response to said varying output audio signal;

a first node and a second node coupled to the second circuit and operable to conduct the electrical pulses through a current conducting circuit created when the first person touches the fist node and makes contact with the second person touching the second node in order to provide a pleasing variable stimulus to the first and second persons; and a switch associated with each of said nodes for adjusting the magnitude of the electrical pulses.

* * * * *